United States Patent [19]

Grollimund et al.

[11] Patent Number: 4,517,825
[45] Date of Patent: May 21, 1985

[54] SELF-CLEANING POROSIMETER

[75] Inventors: Everett C. Grollimund, Midlothian; William H. Smick, III; Donald L. Brookman, both of Richmond, all of Va.

[73] Assignee: Philip Morris Incorporated, New York, N.Y.

[21] Appl. No.: 423,070

[22] Filed: Sep. 24, 1982

[51] Int. Cl.³ .............................................. G01N 15/08
[52] U.S. Cl. ...................................... 73/38; 15/256.53
[58] Field of Search ............... 73/37.6, 38; 15/256.51, 15/256.52, 256.53

[56] References Cited

U.S. PATENT DOCUMENTS

| | | | |
|---|---|---|---|
| 2,323,983 | 7/1943 | Edmondson | 15/256.53 |
| 2,972,767 | 2/1961 | Smith | 15/256.51 |
| 3,056,281 | 10/1962 | Smyth | |
| 3,412,856 | 11/1968 | Esenwein | |
| 3,466,925 | 9/1969 | Ziegenhagen et al. | 73/38 |
| 4,025,752 | 5/1977 | Whitman | |
| 4,121,595 | 10/1978 | Heitmann et al. | |
| 4,246,775 | 1/1981 | Stultz | 73/38 |
| 4,247,754 | 1/1981 | Baier | |

FOREIGN PATENT DOCUMENTS

980058 1/1965 United Kingdom .

Primary Examiner—S. Clement Swisher
Assistant Examiner—Hezron Williams
Attorney, Agent, or Firm—Wayne M. Kennard

[57] ABSTRACT

A high-speed dynamic porosimeter including a device for removing accumulated debris is disclosed. The porosimeter has an apertured surface, preferably curved, across which a web whose porosity is to be measured is drawn while suction is applied to the apertures. A pressure transducer monitors the pressure in a sensor line or chamber, which pressure varies as a function of the porosity of the web. A scraper blade scrapes debris from the apertured surface from time to time. Preferably, vacuum suction is also applied to a slot at the upstream side of the apertured surface to ensure a good seal between the web and the surface.

19 Claims, 12 Drawing Figures

SELF-CLEANING POROSIMETER

BACKGROUND OF THE INVENTION

The present invention pertains to a porosimeter for use in monitoring the porosity of a web of material, and pertains more particularly to such a porosimeter that is capable of cleaning itself periodically to prevent clogging by dust, etc.

It is frequently necessary to maintain the porosity of a web of material constant at a desired value. One application in which this is especally important is the manufacture of cigarette paper, and especially ciagarette tipping paper. In recent years it has become a common practice in the cigarette industry to provide Bands of fine perforations in the paper used to secure the filters to the cigarette rod, each band typically comprising one or more rows of perforation. If the porosity of the tipping paper is not correct within a very narrow tolerance, a cigarette made with the paper will not have the desired characteristics. One system for perforating tipping paper is disclosed in U.S. Pat. No. 4,247,754, issued Jan. 27, 1981, to Baier, for "Apparatus for Perforating Webs of Wrapping Material for Rod-Shaped Smokers Products", and a similar system, including a porosimeter and feedback loop to control the operation of the system, is disclosed in U.S. Pat. No. 4,025,752, issued May 24, 1977, to Whitman, III for "Apparatus for Electrically Perforating Dielectric Webs." Another example of a porosity measuring apparatus is that disclosed in U.S. Pat. No. 4,246,775, issued Jan. 27, 1981, to Stultz, for "Porosity Measuring Apparatus and Perforating System Using Same," assigned in common with the present application and the disclosure of which is incorporated herein by reference.

One type of porosimeter frequently used with tipping paper includes a chamber having a flat surface in which one or more apertures are provided, the web to be tested being pulled across the apertured surface while suction is applied to the apertures. By comparing the pressure in the chamber during this process with the chamber pressure in the absence of the web, it is possible to determine the porosity of the web. One porosimeter of this type is disclosed in U.S. Pat. No. 4,246,775, cited above.

One problem that has been encountered with porosimeters of this type is the accumulation of dust from the web in the porosimeter. The gradual accumulation of such dust can clog the suction lines of the porosimeter, detracting from the accuracy of the device. Debris on the porosimeter surface can also tend to make the location of the web transversely of the direction of motion unstable. It is desirable to provide a porosimeter which avoids this problem altogether. Some known porosimeters also tend to be inaccurate or imprecise when the speed of the web across the porosimeter surface is high or the web tension fluctuates excessively.

SUMMARY OF THE INVENTION

It is the principal object of the invention to provide a porosimeter of the constant flow suction type and of simple design which substantially avoids the problem of dust clogging.

It is another object of the invention to provide a porosimeter of the described type with which it is especially easy to obtain a good seal between a web being tested and the porosimeter.

It is another object of the invention to provide a porosimeter capable of monitoring the porosity of a web moving past the porosimeter at speeds of five to six thousand feet per minute or more.

According to the present invention, a porosimeter of the type described above is provided with a scraper blade, and with means for moving the blade and the apertured porosimeter surface relative to each other to cause the surface to be scraped free of any debris that has collected thereon. In one preferred embodiment, the scraper blade is moved along the surface while the latter is maintained stationary. In another embodiment, the reverse arrangement is used, the knife remaining stationary while the surface is moved so as to be scraped by the blade. In the most preferred embodiment, the scraper blade is contoured to fit the porosimeter surface to be cleaned, and is moved rectilinearly along that surface from time to time to remove accumulated debris. In other embodiments, the porosimeter housing is cylindrical, the sensing slots being provided in the curved lateral surface of the housing. In these cases, the scraper blade is parallel to the axis of the cylinder, and either is rotated about that axis to scrape the porosimeter or is maintained stationary while the porosimeter housing is rotated to effect the scraping.

It is especially common to provide cigarette tipping paper with two parallel bands of small perforations. It is preferable to provide a separate set of sensing apertures in the porosimeter for each band of perforations that have been made in the tipping paper to be examined. Each row of apertures may preferably include a relatively small number (e.g., two or three) of relatively large apertures, or may include a larger number (e.g., up to twenty-four or more) apertures of somewhat smaller dimensions (although there is no inherent upper limit on the number of slots in each row or on the shape of the apertures). In one embodiment, the slots, instead of being parallel to the axis of the cylindrical housing, are helical. With helical slots, it is most preferred that the web should travel about 20 mm. over the slot for optimal performance at high web speeds, although this value is by no means critical.

According to the invention, a positive pressure is preferably provided in the porosimeter at end of the inspection of each roll of paper to blow out any dust that has accumulated inside the sensing slots, and reduce the motor load during acceleration of the web.

Positive pressure is preferably also applied to the web as it begins to move across the apertured surface. This permits the web to float on an air layer, reducing the load on the motor moving the web.

In addition, when the web is moving relatively rapidly, suction is preferably applied to the web at the upstream side of the porosimeter surface. This permits the precise and accurate inspection of a web moving at speeds of several thousand feet per minute.

It has been found that by scraping the surface of the porosimeter after each roll of tipping paper has been examined and before the next roll is inspected, the problem of debris build-up on the surface is eliminated. In addition, the curved shape of the housing makes it possible to obtain an extremely good seal between the web and the porosimeter surface, ensuring a very high degree of accuracy in the data obtained. Moreover, using the slot designs disclosed herein, it has been found that excellent presision can be obtained, even at very high web speeds.

DETAILED DESCRIPTION OF THE PREFERRED EMBODIMENTS

FIGS. 1-6 show a first preferred embodiment of the present invention. The porosimeter 10 of the invention is secured to a vertical base plate 12. One end of the porosimeter body 14 (see FIG. 2), which is roughly cylindrical in shape, is received in an aperture 16 in the base plate 12 and is maintained in place by means of a back plate 18 (see FIG. 2) secured to the body 14 by screws 20. (Hereinafter, "front" and "forward" refer to the end of the porosimeter 10 remote from the back plate 18, while "back", "rear" and "behind" refer to the end of the porosimeter 10 near the plate 18.) Apertures 60 (see FIG. 2) are provided in a portion of the cylindrical porosimeter. It is usual in the manufacture of cigarettes to manufacture filter cigarettes in pairs, attached end-to-end by their filters, and then to sever the two cigarettes from each other. The tipping paper, which is applied to the filter plug before the separation of the cigarettes, is symmetric and may typically have two parallel bands of perforations, one band for each cigarette. To measure the porosity of a web 11 of such tipping paper, the web 11, having two bands of perforations 13, is wrapped partway around the porosimeter to cover the apertures 60 and is pulled across the apertured surface to enable the porosity of the entire length of web 11 to be measured dynamically. As can be seen, the two portions of the web 11 having the perforations 13 are passed over respective rows of the apertures 60 of the porosimeter 10.

Figure 1:
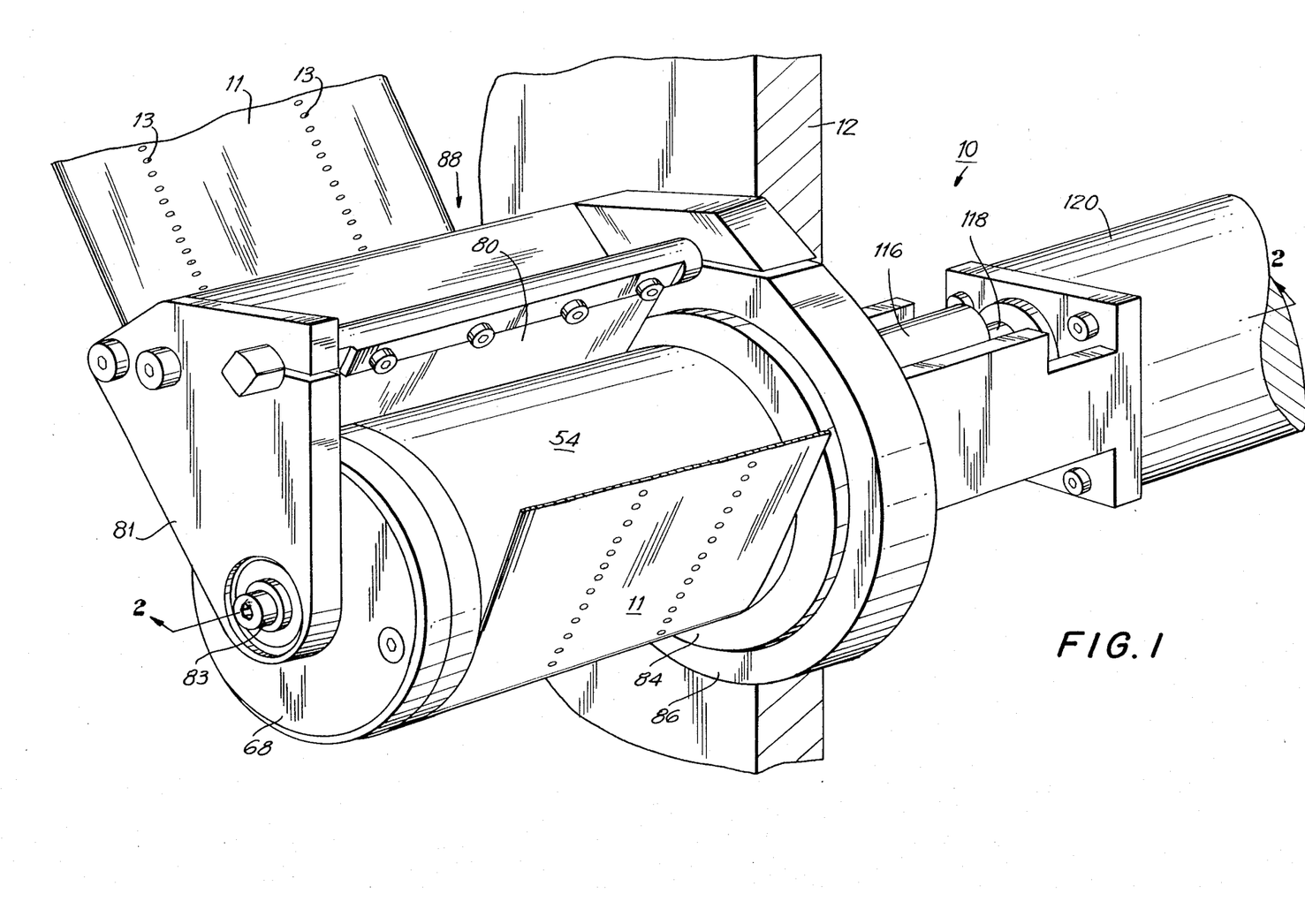
FIG. 1 is a perspective view of a first preferred embodiment of the porosimeter of the invention.
Figure 2:
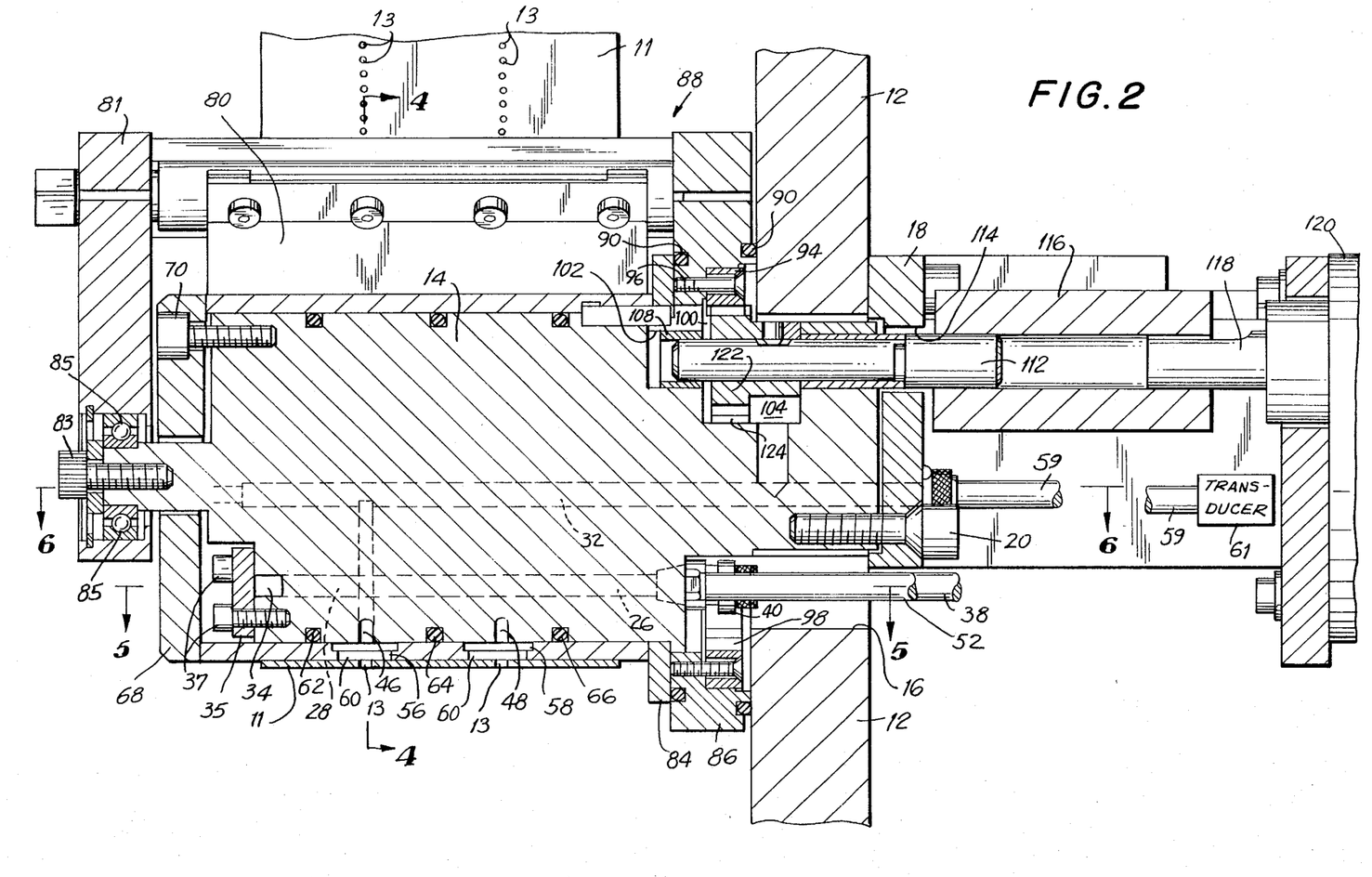
FIG. 2 is a longitudinal cross-sectional view of the porosimeter of FIG. 1, taken from section line 2—2 in FIG. 1.
Figure 3:
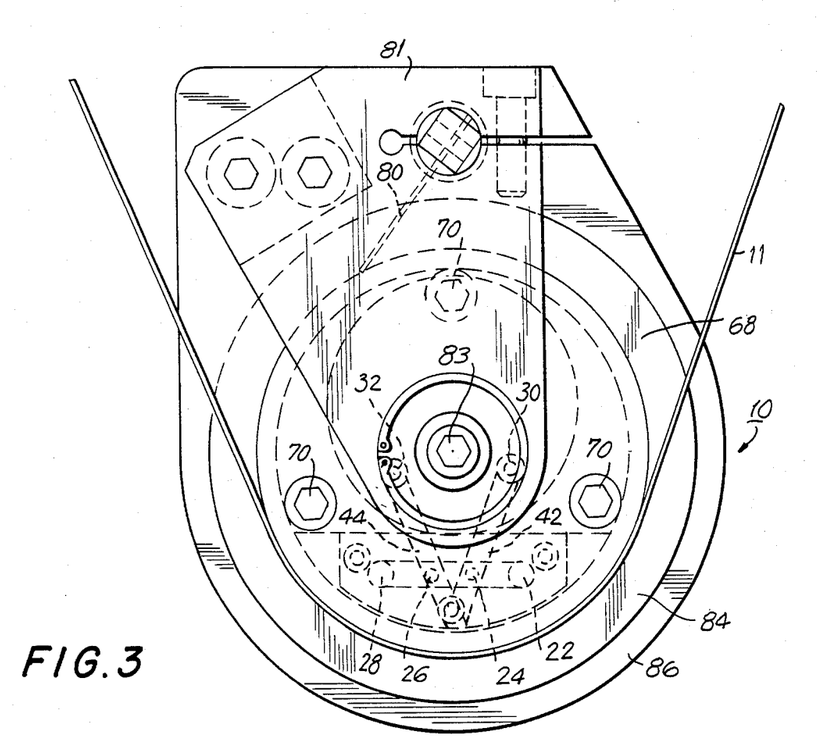
FIG. 3 is an end view of the porosimeter of FIG. 1.
Figure 4:
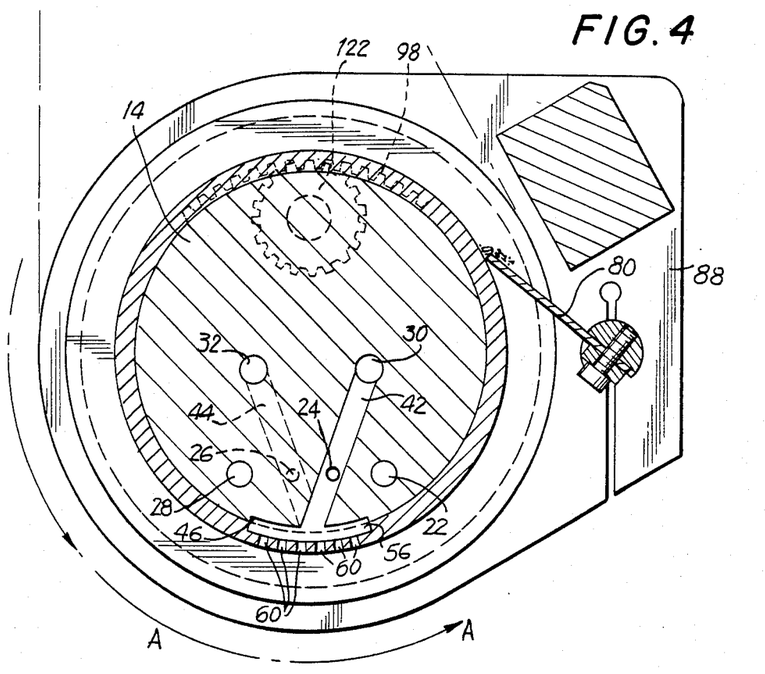
FIG. 4 is a cross-sectional view taken from section line 4—4 in FIG. 2.
Figure 5:
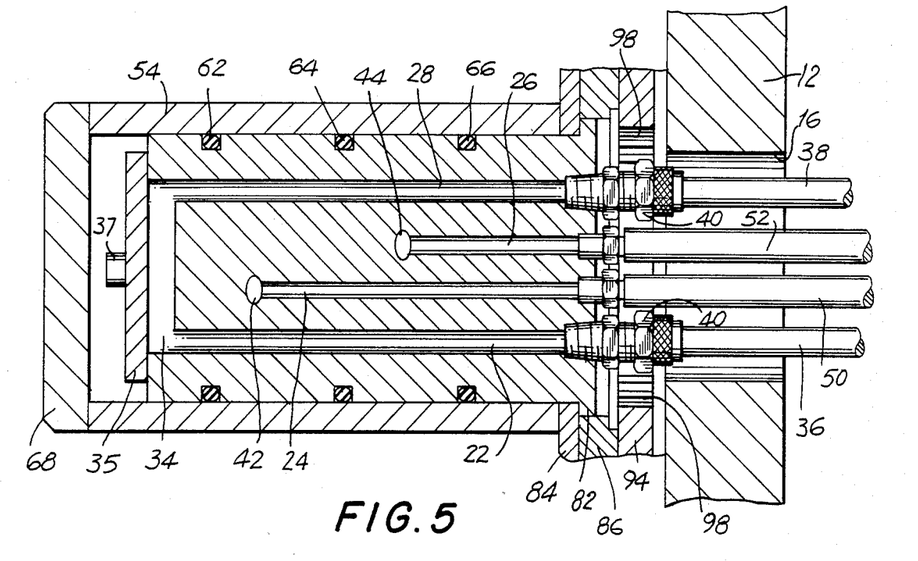
FIG. 5 is a cross-sectional view taken from section line 5—5 in FIG. 2.
Figure 6:
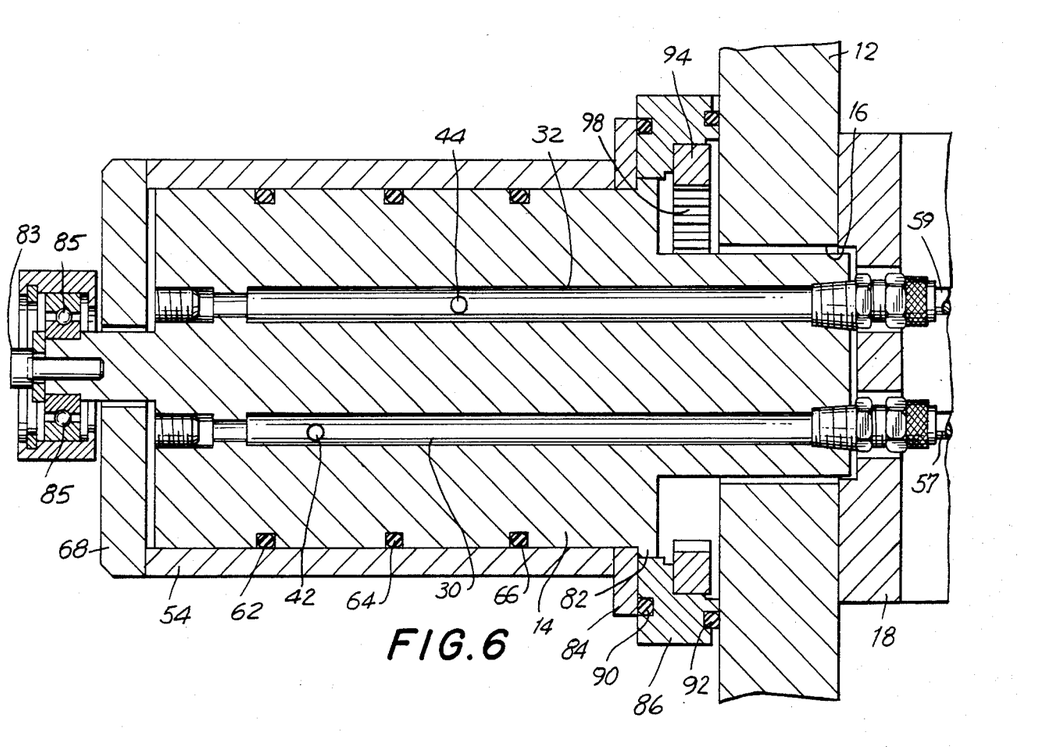
FIG. 6 is a cross-sectional view taken from section line 6—6 in FIG. 2.

The number of rows of slots 60 preferably equals the number of bands of perforations 13 in the webs with which it is contemplated the porosimeter 10 will be used.

After a roll of material has been inspected, the apertured surface of the porosimeter is scraped clean of dust and similar debris that has accumulated on the surface. This is effected by means of a scraper blade 80 mounted for movement around the cylindrical surface of the porosimeter 10, powered by a motor 120.

Six cylindrical bores 22, 24, 26, 28, 30, 32, four lying in one horizontal plane and two in a second plane, are provided in the porosimeter body 14 parallel to the axis thereof. Bores 22, 28 can be used for carrying a coolant liquid to the porosimeter 10, should this be necessary to remove the heat generated by movement of the web 11 across the surface of the porosimeter 10, and communicate with each other via a cavity 34 at the front end of the porosimeter 10 (see FIGS. 2 and 5). A plate 35 closes the front end of the front cavity 34, and is secured to the porosimeter body 14 by means of screws 37. Lines 36, 38 for the supply and removal of the coolant fluid pass through the lower portion of the aperture 16 of the base plate 12 and are secured to bores 22, 28 by means of nuts 40.

Bores 24, 26 provide the constant flow suction for the operation of the porosimeter 10. Each of bores 24, 26 extends part way along the length of the porosimeter body 14, and terminates in a junction with a respective inclined conduit 42, 44 which connects its bore 24, 26 with a respective upper bore 30, 32 and with a respective circumferential slot-like aperture 46, 48 in the lower surface of the porosimeter body 14. Suction lines 50, 52 for applying suction to bores 24, 26 are also accommodated in the aperture 16 in the base plate 12.

The porosimeter 10 includes a cylindrical shell 54 surrounding the central body 14. The cylindrical shell 54 is held in place by a front plate 68, which is secured by means of screws 70 to the porosimeter body 14. The lower surface of the shell 54 has, on its internal surface, two parallel milled passages 56, 58 which proceed partway around the circumference of the shell 54 and communicate with the apertures 46, 48 in the lower portion of the porosimeter body 14. The apertures 60 in the outer surface of the cylindrical shell 54 communicate with the milled passages 56, 58. In order to prevent leakage in the vacuum systems, three O-rings 62, 64, 66 are provided in circumferential grooves in the porosimeter body 14, one ahead of the two apertures 46, 48 one behind them and one between them.

In operation, vacuum suction is applied to the suction lines 50, 52 while a web 11 of material wrapped partway around the outer surface of the cylindrical shell 54 over the apertures 60 is pulled across the surface. Lines 57, 59 attached to the sensor bores 30, 32 are connected to high-speed pressure transducers 61 (indicated schematically in FIG. 2) which produce electrical signals responsive to the pressure observed. (Any conventional transducer could be used, although not all are equally suitable for use at high web speeds.) The signals are analyzed to provide an indication on a meter or a recording device (not shown) or the like of the porosity of the web 11.

One transducer suitable for use in the preferred embodiments, even at very high web speeds (e.g., 5–6,000 feet per minute) is the Validyne P-305D-26 reluctance-principle transducer, in which a conductive diaphragm between the two windings of a transformer flexes as a function of pressure, varying the signals appearing at the transformer terminals.

For the required degree of precision, very slight variations in pressure must be detectable.

The scraper blade 80 is mounted so as to lie against the shell 54 at an acute angle to the shell surface. In the embodiment of FIGS. 1-6, the blade 80 is mounted to be rotatable about the axis of the porosimeter 10 in order to scrape the entire lateral surface thereof.

The front end of the scraper blade 80 is secured to a front mount plate 81, which is secured by a screw 83 to the front end of the porosimeter body 14. Bearings 85 are provided between the front mount plate 81 and the porosimeter body 14 to permit their relative rotation.

An annular radial flange 82 is provided on the porosimeter body 14 and serves as a shoulder to receive an annular collar 84. The latter serves as a shoulder on which to receive the cylindrical shell 54. Between the collar 84 and the base plate 12 is a second collar 86 of L-shaped cross-section. One end of the scraper blade mount 88 is secured to the external surface of the second collar 86. Recesses containing O-rings 90, 92 are provided in the front and back surfaces of the second collar 86, providing sealing between the first collar 84, the second collar 86 and the base plate 12 to exclude debris. The internal angle of the L-shape of the second collar's cross-section serves as a shoulder to receive another annular collar 94, secured to the second collar 86 by means of screws 96. The internal surface of the third collar 94 is provided with gear teeth 98.

A cylindrical bore 100 is provided in the back surface of the porosimeter body 14 parallel to the axis thereof. The axially middle portion 102 of the bore 100 has a larger diameter than the end portions 104, 106. Both end portions 104, 106 receive respective sleeves 108, 110, which support a pin 112. One end of the pin 112 extends through an aperture 114 provided for it in the back plate 18 and is received securely in a sleeve 116 the other end of which receives the drive shaft 118 of the motor 120. A gear 122 is secured to the pin 112 for rotation therewith and is received in the large-diameter middle portion 102 of the bore 100. The gear 122 has the form of a cylindrical collar mounted on the pin 112 and is provided with teeth 124 defined in its forward portion of its lateral surface to engage the gear teeth 98 on the internal surface of the third collar 94. The motor 120, by rotating the pin 112 and the gear 122 mounted thereon, causes rotation of the second collar 86 about the axis of the porosimeter 10, causing the blade 80 to scrape the surface of the cylindrical shell 54.

In operation, as already explained, a web 11 is passed over the apertures 60 in the cylindrical porosimeter while suction is applied to the suction lines 50, 52. After a roll of paper has been inspected and before the next roll is examined, the motor 120 is actuated to rotate the scraper blade 80 around the perimeter of the cylindrical shell 54, as indicated by arrows A in FIG. 4, scraping dust and other particulate matter therefrom.

In order to prevent excessive dust build-up inside the porosimeter and the attendant problems of clogging and inaccurate operation, as well as to reduce unnecessary loading of the motor 120, a positive pressure, preferably on the order of 60-80 psi above ambient pressure, is developed in the porosimeter interior via the suction lines 50, 52 after examination of each roll has been completed, to blow out any dirt that has accumulated in the interior of the porosimeter 10. The positive pressure is then reduced to 2-3 psi until a new bobbin of paper is in place for inspection and has been accelerated by the web-pulling motor (not shown, and not to be confused with the motor 120) to a reasonable fraction (most preferably at least 60-68%) of operating speed. This positive pressure reduces friction by providing an air cushion for the web.

Figure 7:
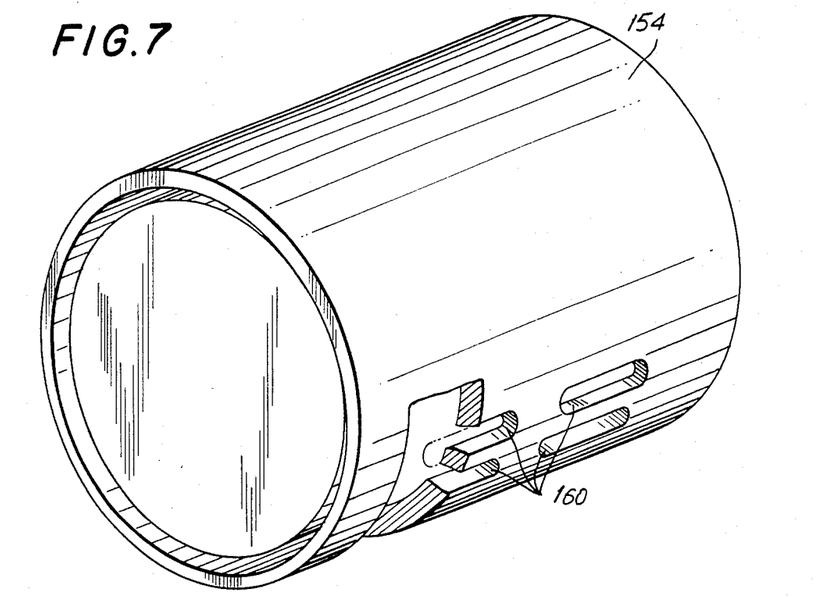
FIG. 7 is a view showing the slot arrangement in a second preferred embodiment.
Figure 8:
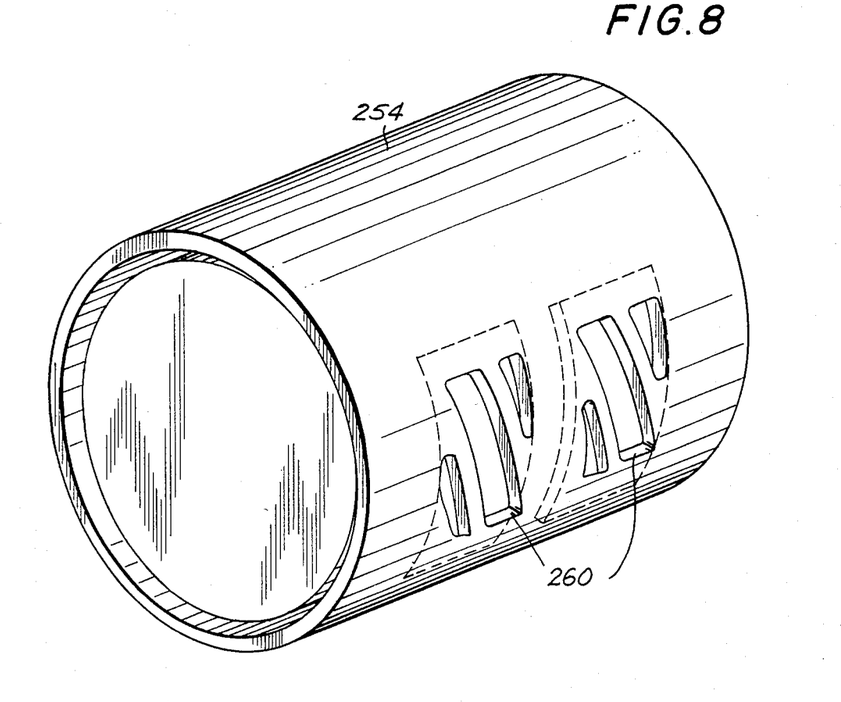
FIG. 8 is a view showing the slot arrangement of a third preferred embodiment, having helical slots.

FIGS. 7 and 8 show different embodiments of the cylindrical shell 154, 254 of the porosimeter, in which differing numbers and shapes of apertures 160, 260 are provided. A small number of relatively large slots (e.g., one or two) may be provided in each row, or a larger number (e.g., twenty-four) of smaller slots may be provided. Any number within these limits is suitable, and there is no inherent upper limit on the number that can used successfully. It is, however, desirable that no single slot should be too large, lest the web be wrinkled as a result of the suction. Conversely, if the slots are too small, it will be difficult to get the desired sensitivity. The illustrated arrangements avoid both of these problems.

In the embodiment shown in FIG. 8, the slots 260 are helical rather than parallel to the axis of the porosimeter. It has been found that particularly good results are obtained if helical slots 260 having a width (measured parallel to the direction of the web's movement) of about 20 mm. are used. (Equally good, or even slightly better, results have been obtained using slots measuring 30 mm. in this dimension, but in this case the total area of contact between the web and the porosimeter surface is substantially greater than is necessary with 20 mm. slots, increasing the load on the web-pulling motor correspondingly.) With such slots and rapid-response reluctanceprinciple transducers, it is possible to measure porosity accurately at web speeds as high as 5,000-6,000 feet per minute. It is believed that these excellent results are obtained with helical slots of the stated size because the web 11 is exposed to the porosimeter suction for a relatively long time (because of the relatively great width of the slots). It is to be specifically understood that the scope of the invention is limited neither to the size nor to the shape of the slots of the preferred embodiments.

Figure 9:
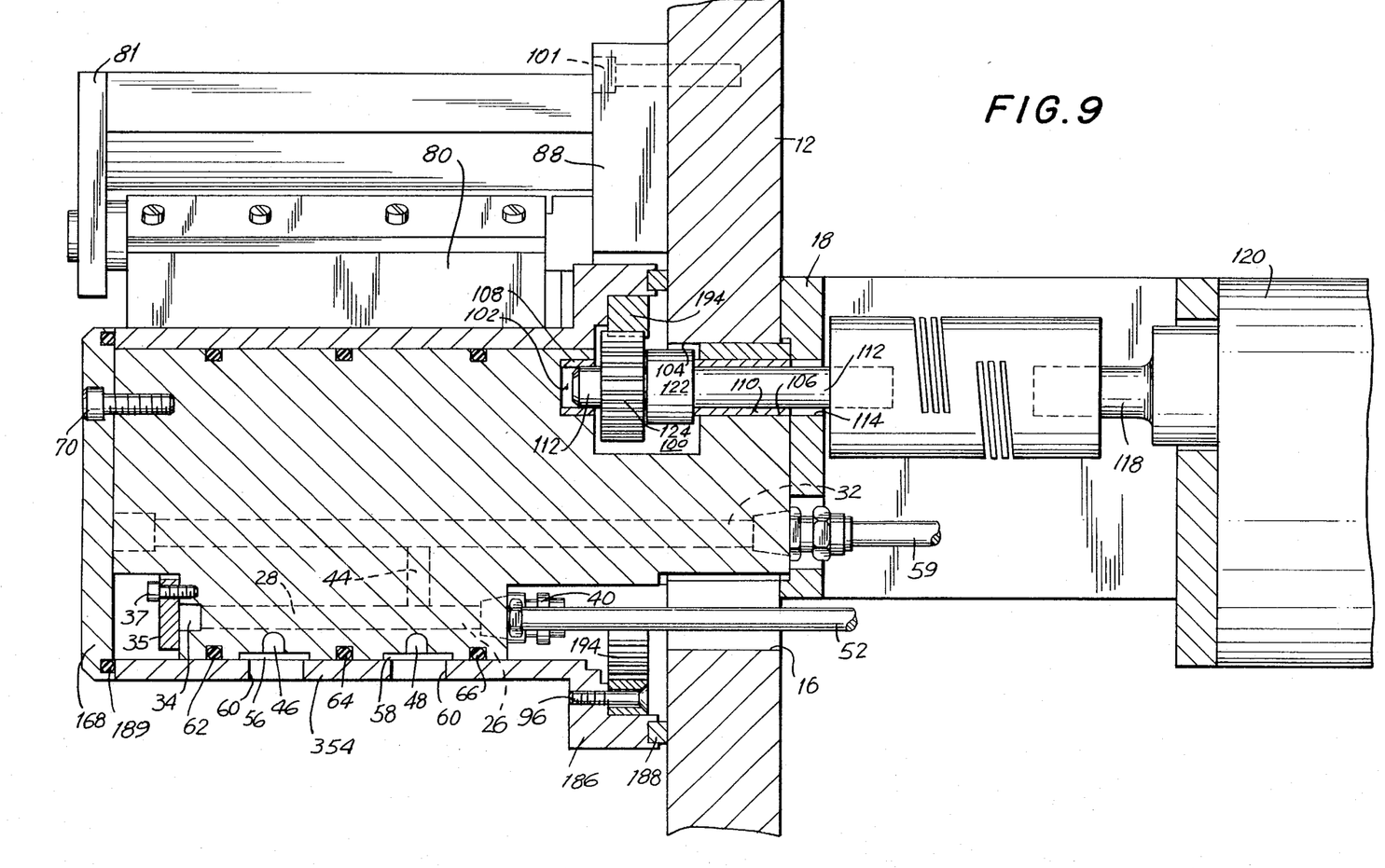
FIG. 9 is a longitudinal cross-section, corresponding to the view of FIG. 2, of a fourth preferred embodiment, in which the scraper blade is stationary.

The embodiment of FIG. 9 is similar to that shown in FIGS. 1-6, except that the scraper blade 80 is secured by means of bolts 101 to plate 12 in the embodiment of FIG. 9, so as to remain stationary, while the motor 120 is connected to the porosimeter body 14 via the toothed collar 194 to rotate the porosimeter body 14 together with the attached cylindrical shell 354. In this embodiment, the collar 186 having the L-shaped cross-section and fixedly receiving the toothed collar 194 on the shoulder defined by its interior surface is preferrably integral with the cylindrical shell 354. A seal between the collar 186 and plate 12 is provided by a seal ring 188 received between the collar 186 and the plate 12. Another seal ring 189 is also provided between the porosimeter front plate 168 and the shell 354. If very small variations in pressure must be detectable, this embodiment is somewhat less suitable than that shown in FIGS. 1-5 because of the somewhat greater difficulty of maintaining the air-tight seals intact, since the rotation of the porosimeter body tends to impair the seal. Nonetheless, this embodiment is also within the scope of the invention.

Figure 10:
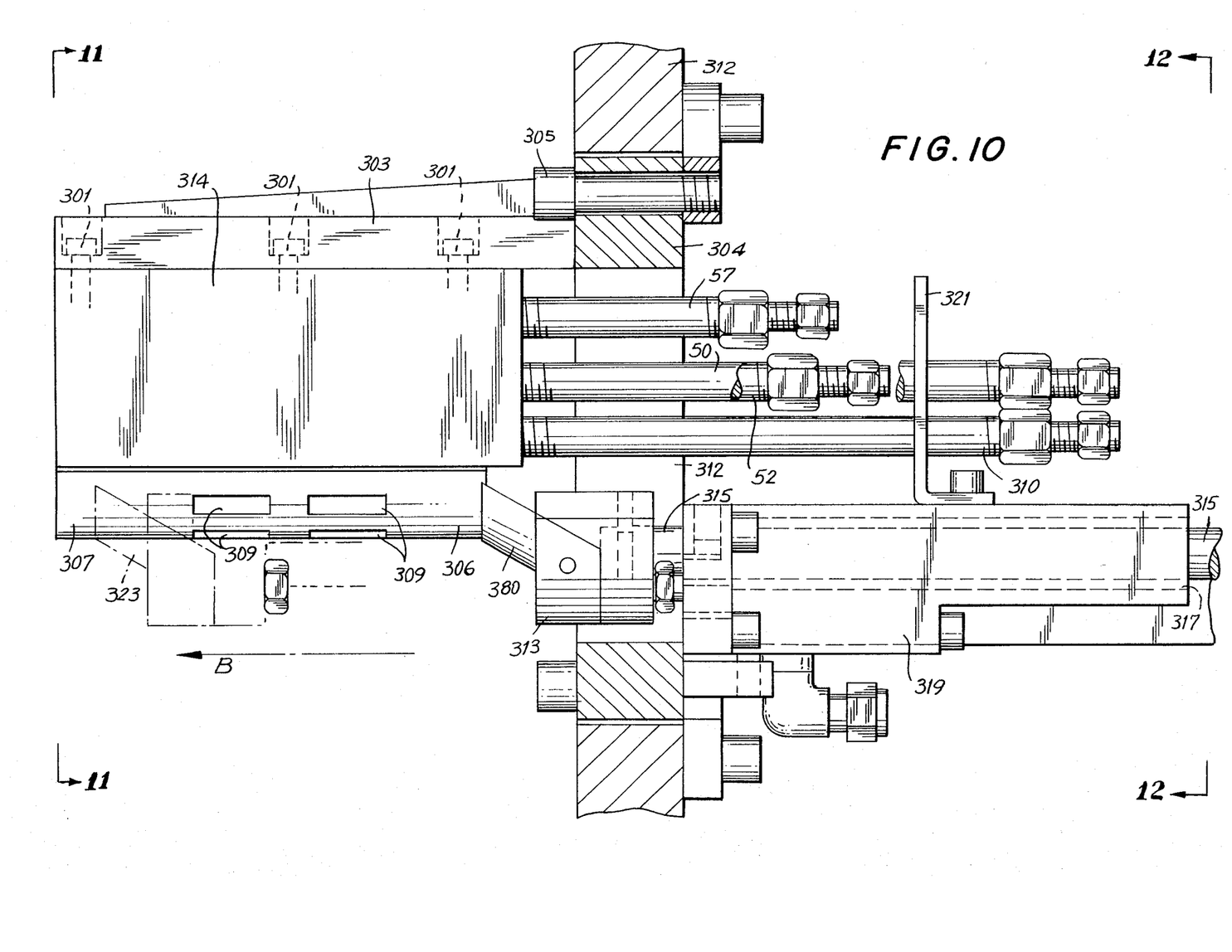
FIG. 10 is a side view, partly in section, of a fifth preferred embodiment.
Figure 11:
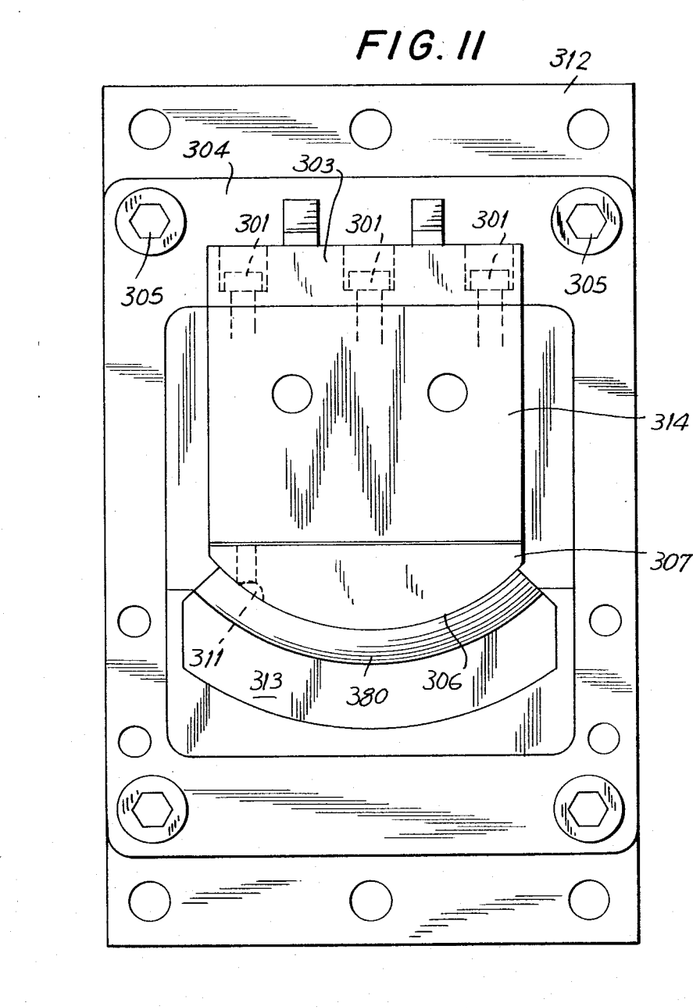
FIGS. 11 and 12 are end views of the embodiment of FIG. 10, taken from lines 11—11 and 12—12 in FIG. 10, respectively.
Figure 12:
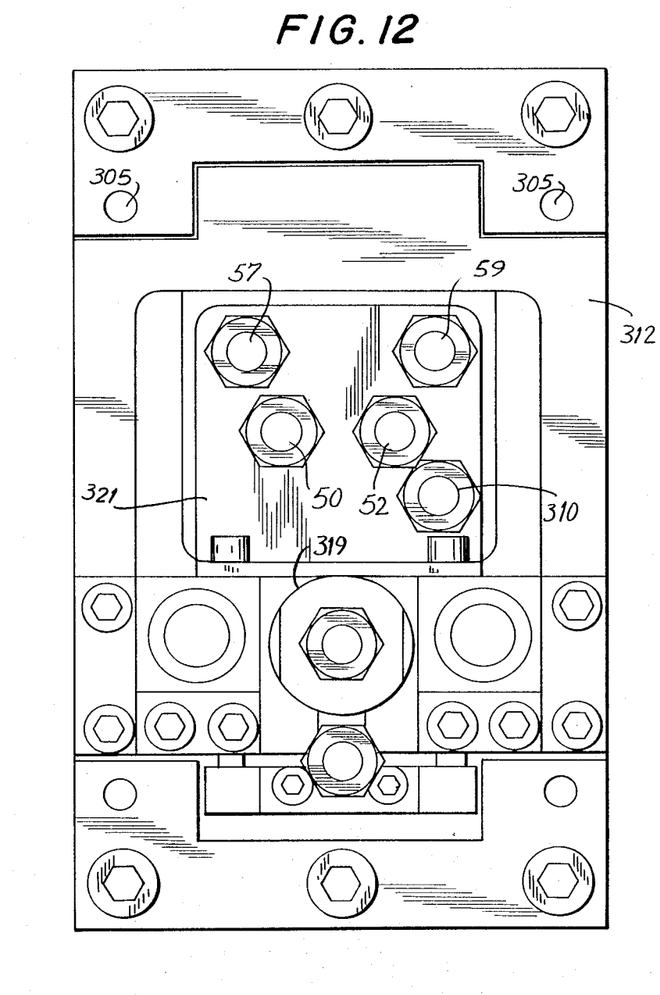

FIGS. 10-12 show another preferred embodiment in which the porosimeter is non-cylindrical and the scraper blade 380 follows a rectilinear path, as indicated by the arrow B. In this embodiment, the top of the porosimeter body 314 is secured by bolts 301 to a flat plate 303 projecting from a generally rectangular collar 304, which, in turn, is secured by bolts 305 to a base plate 312. The surface 306 across which the web is drawn is defined by a metal block 307 and is curved, although it is not necessarily cylindrical in curvature. The block 307 has the sensing apertures 309 defined in it. In addition to suction and sensing bores and corresponding lines 50, 52, 57, 59 much the same as those of the embodiment of FIGS. 1-6, the embodiment of FIGS. 10-12 has a line 310 for applying vacuum suction to a web being drawn across the surface 306 via a suitable additional longitudinal bore (not shown) in the porisimeter body 314 and a vacuum slot 311 (see FIG. 11) defined near one edge of surface 306 and oriented transverse to the direction of the web's movement. As the web is moved across the surface 306 from the side adjacent the slot 311, the suction exerted on the web via the slot 311 holds the web against the surface 306. This greatly increases the speed at which the web can be inspected. Without the vacuum slot 311, it has been found that accurate measurement of web porosity is impossible at web speeds over about 1200 feet per minute; however, with the suction provided via the slot 311, the porosimeter of the invention will function properly at speeds up to at least 5,000-6,000 feet per minute. It is believed that the reason for this is that at high web speeds, the web pulls air between the web and the surface 306. The resulting air layer between the web and surface 306, if not removed by means of vacuum suction via slot 311, prevents accurate measurement of the web's porosity. Although such a suction mechanism is not shown in all of the illustrated embodiments, this feature can be, and preferably is, included in every embodiment.

To clear the surface 306, a scraper blade 380 whose edge has the same shape as the transverse cross-section of the surface 306 is provided. The scraper blade 380 is secured to a semi-annular blade holder 313, which is mounted to one end of a rod 315 that is slidably received in a bore 317 of a block 319 secured to the base plate 312. A bracket 321 secured to the block 319 has apertures receiving the lines 50, 52, 57, 59, 309. Actuation of a suitable motor (not shonw) slides the rod 315 along the bore 317, causing the scraper blade 380 to scrape the length of the surface 306, as indicated in phantom at 323 in FIG. 10. The rod 315 is then retracted.

In using any embodiment of the invention, the motor can be manually actuated by an operator after each bobbin of paper or the like has been examined. After becoming familiar with the present invention as disclosed herein, however, it is within the skill of one of average skill in the art, using standard commercially available components, to provide an automatic control system to detect completion of one bobbin, actuate the motor 120 to clean the porosimeter, deactivate the motor 120, actuate the pressure source to provide the described positive pressure, and then replace the positive pressure with suction once the next bobbin has been mounted and accelerated to about 60-68% of operating speed. One commercially available programmable control unit that has been found suitable for this application is the Gould/Modicon C484-165 Enhanced I unit. It should be noted, however, that such an automatic control system forms no part of the present invention, which is limited to a porosimeter as claimed.

The specific embodiments described herein are merely illustrative of the present invention, the true scope of which is set forth in and is to be determined solely by the terms of the appended claims.

What is claimed is:

1. A self-cleaning porosimeter, comprising:
   a housing having a surface, said surface having aperture means defined therein;
   suction means for applying suction to said aperture means to exert suction on a web lying against and moving along said surface, the pressure in at least part of said suction means varying as a function of the porosity of the web surface;
   transducer means for producing a signal representative of the porosity of the web responsive to said pressure in said suction means;
   rigid blade means for lifting material adhering to said surface from said surface; and
   motor means for causing relative motion of said blade means and said surface for causing said blade means to clean said surface by said relative motion.

2. The porosimeter of claim 1, wherein said motor means is for moving said blade means along said surface.

3. The porosimeter of claim 2, wherein said housing is generally cylindrical, and wherein said motor means is for moving said blade means along said surface about the axis of said housing.

4. The porosimeter of claim 1, wherein said motor means is for moving said housing to cause said relative motion.

5. The porosimeter of claim 4, wherein said housing is generally cylindrical, and wherein said motor means is for rotating said housing to effect said relative motion.

6. The porosimeter of claim 1, 2 or 4, wherein said aperture means includes a plurality of apertures disposed in a row along a direction of intended web movement along said surface.

7. The porosimeter of claim 6, wherein said aperture means comprises at least two such rows of apertures.

8. The porosimeter of claim 1, 2 or 4, wherein said aperture means comprises a plurality of helical grooves.

9. The porosimeter of claim 1, wherein said surface has a predetermined cross-sectional shape, and wherein said blade means is contoured to fit said shape, said motor means being for moving said blade means along said surface.

10. The porosimeter of claim 9, wherein said motor means is for moving said blade means rectilinearly.

11. The porosimeter of claim 1, further comprising means for removing air from between a moving web and said surface when said moving web moves along said surface causing said web to be directly in contact with said surface at a position along said surface after said moving web passes said means.

12. The porosimeter of claim 11, wherein said means for removing air from beteeen said moving web and said surface comprises means for removing air from between said surface by applying suction to at least a portion of the width of said web moving along said surface.

13. A dynamic porosimeter, comprising:
   a housing having a curved surface, said surface having aperture means defined therein;
   suction means for applying suction to said aperture means to exert suction on a web moving along said surface, the pressure in at least part of said suction means varying as a function of the porosity of the web;
   transducer means producing a signal representative of the porosity of the web responsive to said pressure; and
   means for removing air from between said moving web and said surface when said web moves along said surface causing said web to be in direct contact with said surface at a position along said surface after said moving web passes said means for removing air from between said moving web and said surface.

14. The porosimeter of claim 13, wherein said second suction means comprises means for applying suction to a web moving across said surface, at a point adjacent said aperture means.

15. The porosimeter of claim 1 or claim 13, wherein said transducer means comprises a reluctanceprinciple transducer.

16. The porosimeter of claim 1 or claim 13, further comprising means for providing air inside said porosimeter at a higher-than-ambient pressure for cleaning said aperture means.

17. The porosimeter of claim 1 or claim 13, further comprising means for providing air adjacent said surface at a higher-than-ambient pressure for reducing friction between said surface and a web moving thereacross.

18. The porosimeter of claim 17, wherein said air providing means is for producing higher-than-ambient pressure in said aperture means.

19. The porosimeter of claim 8, wherein each said helical groove has a width, as measured in the direction of intended movement of a web thereacross, of about 20 millimeters.

* * * * *

UNITED STATES PATENT AND TRADEMARK OFFICE
CERTIFICATE OF CORRECTION

PATENT NO. : 4,517,825

DATED : May 21, 1985

INVENTOR(S) : Everett C. Grollimund, et al

It is certified that error appears in the above-identified patent and that said Letters Patent is hereby corrected as shown below:

Title page:

The following prior art references of record should be listed:

| U.S. Patent No. | Month/Year of Issue | Patentee | Class/Subclass |
|---|---|---|---|
| 3,371,518 | 3/1968 | Keyes | 73/38 |
| 3,439,536 | 4/1969 | Cushman | 73/38 |
| 3,624,860 | 12/1971 | Grimston et al | 15/256.51 |
| 3,740,789 | 6/1973 | Ticknor | 15/256.53 |
| 3,835,779 | 9/1974 | Ross et al | 15/256.52 |
| 3,893,813 | 10/1976 | Tani | 15/256.53 |

Column 10, line 2, "mcans" should be -- means --.

Signed and Sealed this

Fourth Day of November, 1986

[SEAL]

Attest:

DONALD J. QUIGG

Attesting Officer

Commissioner of Patents and Trademarks